US008119160B2

(12) United States Patent
Looney et al.

(10) Patent No.: US 8,119,160 B2
(45) Date of Patent: Feb. 21, 2012

(54) HEMOSTATIC COMPOSITIONS AND DEVICES

(75) Inventors: Dwayne Lee Looney, Flemington, NJ (US); Guanghui Zhang, Belle Mead, NJ (US); Sonia Martins, Elizabeth, NJ (US)

(73) Assignee: Ethicon, Inc., Somerville, NJ (US)

( * ) Notice: Subject to any disclaimer, the term of this patent is extended or adjusted under 35 U.S.C. 154(b) by 1348 days.

(21) Appl. No.: 11/078,049

(22) Filed: Mar. 11, 2005

(65) Prior Publication Data

US 2005/0284809 A1 Dec. 29, 2005

Related U.S. Application Data

(63) Continuation-in-part of application No. 10/880,654, filed on Jun. 29, 2004, now abandoned.

(51) Int. Cl.
  *A61K 9/16* (2006.01)
  *B01D 39/00* (2006.01)
  *B01D 15/00* (2006.01)

(52) U.S. Cl. ............... 424/485; 210/502.1; 210/263

(58) Field of Classification Search ............ 424/485
See application file for complete search history.

(56) References Cited

U.S. PATENT DOCUMENTS

| | | | |
|---|---|---|---|
| 2,507,244 A | | 5/1950 | Correll et al. |
| 4,407,787 A | * | 10/1983 | Stemberger .............. 424/444 |
| 5,733,572 A | | 3/1998 | Unger et al. |
| 5,908,054 A | | 6/1999 | Safabash et al. |
| 6,045,570 A | | 4/2000 | Epstein et al. |
| 6,063,061 A | | 5/2000 | Wallace et al. |
| 6,066,325 A | | 5/2000 | Wallace et al. |
| 6,482,179 B1 | * | 11/2002 | Chu et al. ............... 604/164.09 |
| 2002/0193448 A1 | | 12/2002 | Wallace et al. |
| 2002/0197302 A1 | | 12/2002 | Cochrum et al. |
| 2003/0064109 A1 | | 4/2003 | Qian et al. |
| 2003/0162708 A1 | * | 8/2003 | Wolff .......................... 514/12 |

FOREIGN PATENT DOCUMENTS

| | | |
|---|---|---|
| EP | 0372966 A | 6/1990 |
| EP | 0740528 B1 | 11/1994 |
| EP | 0927053 B1 | 4/2003 |
| WO | WO 98/08550 A1 | 3/1998 |
| WO | WO 00/76533 A1 | 12/2000 |
| WO | WO 01/97826 A2 | 12/2001 |
| WO | WO 0197873 A2 | 12/2001 |
| WO | WO 02/072128 A1 | 9/2002 |
| WO | WO 03/007845 A1 | 1/2003 |
| WO | WO 03/055531 A2 | 7/2003 |

OTHER PUBLICATIONS

Westermarck, S. 'Use of Mercury Porosimetry and Nitrogen Adsorption in Characterisation of the Pore Structure of Mannitol and Microcrystalline Cellulose Powders, Granules and Talbets' Academic Dissertation, University of Helsinki, Finland, Nov. 2000 (Abstract).

Sakurabayashi, "Clinical Evaluation of New Hemostatic Agent for Hemostasis From Biopsy Wounds in the Liver" *Gastroenterological Endoscopy*, vol. 30(10). (Oct. 1988) pp. 2256.

European Search Report dated Dec. 22, 2005 for corresponding Appln. No. EP 05254033.

* cited by examiner

*Primary Examiner* — Sreeni Padmanabhan
*Assistant Examiner* — Timothy E Betton
(74) *Attorney, Agent, or Firm* — David R. Crichton

(57) ABSTRACT

The present inventions includes a plurality of packed particles that contain interstitial pores, where the interstitial pores have a pore volume and a median pore diameter effective to provide improved absorption of physiological fluids or an aqueous media when placed in contact therewith, compared to a plurality of unpacked particles of the same material, where the particles are made of a biocompatible material and hemostatic agents and have an average diameter suitable for use in providing hemostasis to a site of a body of a mammal requiring hemostasis, hemostatic compositions containing such plurality of packed particles, methods of making such particles and compositions and medical devices suitable for delivering and containing the hemostatic plurality of particles and/or composition to a site of a body.

10 Claims, 7 Drawing Sheets

HEMOSTATIC COMPOSITIONS AND DEVICES

This application is a Continuation-In-Part of application Ser. No. 10/880,654, filed Jun. 29, 2004 now abandoned.

FIELD OF THE INVENTION

The present invention relates to a plurality of packed particles of a biocompatible material suitable for providing hemostasis to a site of the body requiring hemostasis, hemostatic compositions and medical devices containing such particles and methods for making such packed particles.

BACKGROUND OF THE INVENTION

Protein-based hemostatic materials such as collagen and gelatin are commercially available in solid sponge, fibrillar and loose or unpacked powder form for use in surgical procedures. Mixing of the loose or unpacked powder with a fluid such as saline or thrombin may form a paste or slurry that is useful as a hemostatic composition for use in cases of diffuse bleeding, particularly from uneven surfaces or hard to reach areas, depending on mixing conditions and relative ratios of the materials.

Conventional slurries are prepared at the point of use by mechanical agitation and mixing of loose powder and liquid to provide uniformity of the composition. Mixing of the powder and fluid may be conducted in a container, such as a beaker. Such mixing requires transfer of the powder from its original container to the beaker, addition of the fluid to the beaker containing the powder, and then kneading of the mixture to form the paste. Only after the paste is thus formed may the paste be placed into a delivery means or applicator, e.g. a syringe, and applied to the wound. Alternately, attempts have been made to preload one syringe (Syringe I) with loose gelatin powder, and a second syringe (Syringe II) with liquid. When it is time to make a paste, Syringes I and II are connected via a luer lock and the solution in Syringe II is pushed into Syringe I. By attempting to pass the solution and powder repeatedly back and forth between Syringes I and II, a homogeneous paste may or may not be formed. Often in a surgical situation, a hemostatic paste with optimal powder:liquid ratio cannot be obtained due to insufficient mixing of the powder and the liquid in a syringe. When the powder is first mixed with a liquid, the powder hydrates rapidly to form a gel, thus blocking any further penetration of liquid into the mass of powder. Therefore, a homogeneous paste may not be achieved. Even if such methods of mixing are successful in forming a paste, the time and mechanical effort required to form the paste are undesirable or even unacceptable.

Such mixing procedures and manipulations are time consuming and potentially may compromise the sterility of the hemostatic paste. It would be desirable if a hemostatic composition could be provided which would eliminate the need for such undesirable mixing conditions. The present inventions provide a plurality of packed particles and compositions that more readily absorb aqueous liquids, such that undesirable mixing requirements as noted above are not required in order to form flowable hemostatic slurries, and/or that more readily absorb physiological fluids when placed at a site in the body of a mammal requiring hemostasis.

SUMMARY

The invention is directed to a plurality of packed particles having interstitial pores, where the interstitial pores have a pore volume and a median pore diameter effective to provide improved absorption of physiological fluids or an aqueous media into the interstitial pores when placed in contact therewith, compared to a plurality of unpacked particles of the same composition, and where the particles are made from a biocompatible material and have an average diameter suitable for use in providing hemostasis to a site of a body of a mammal requiring hemostasis, to hemostatic compositions containing such plurality of packed particles, to methods of making the plurality of packed particles and to medical devices containing and suitable for delivering such plurality of packed particles and compositions to a site requiring hemostasis.

DETAILED DESCRIPTION OF THE INVENTION

Figure 1:
FIG. 1 is an image produced by scanning electron microscopy (500×) of a collagen particle.

As used herein, "compressed" and "condensed" are used in the ordinary meaning of those words in the context of standard nomenclature used to define and describe the density of the powders. Condensed and packed are used interchangeably herein. As used herein, "sterile" means substantially free of living germs and/or microorganisms and as further recognized and described by governmental standards pertaining to compositions and medical devices described and claimed herein. As used herein, "hemostatic", or "hemostatic properties", means the ability to stop or minimize bleeding, as one skilled in the art of hemostasis would understand those terms to mean, and as further exemplified in the examples of the specification.

In certain embodiments, the present invention is directed to a plurality of particles of a biocompatible material suitable for use in providing hemostasis to a body site of a mammal requiring hemostasis and to compositions that are effective for providing hemostasis to a body site of a mammal requiring hemostasis and that comprise the plurality of particles of the invention. The plurality of particles are packed together, for example by compression, to form a structure, or body, comprising the plurality of particles that have been packed together such that interstitial pores, or channels, are created within the plurality of packed particles. The terms interstitial pores and interstitial channels are used interchangeably herein. Upon compression of the loose particles together, the spaces between the unpacked, loose particles are reduced, thus forming the interstitial pores or channels. The pores provide a particular pore volume in the plurality of packed particles. It is noted that the particles themselves are substantially non-porous and do not appreciably contribute to the pore volume. However, the particles may be folded upon themselves upon compression to form pores contributing to the overall pore volume.

The median pore diameter of the interstitial pores is effective to facilitate hydration of the packed particles when placed in contact with liquids in which the particles are substantially insoluble, e.g. physiological fluids or an aqueous solution such as saline, by improving penetration or absorption of the liquid into the interstitial pores, when compared to the absorption of the same liquid into a plurality of particles of the same material that have not been compressed or packed together. While not intended to limit the scope of the invention, it is believed that the liquids are drawn rapidly into the channels to wet the particles by a phenomenon called capillary flow.

Capillary flow takes advantage of water's nature of prevalent hydrogen bonding. The hydrogen-bonding nature of water gives rise to its high cohesiveness and its high surface tension. When water is in contact with a capillary with a hydrophilic surface, the capillary flow overrides gravity and can occur in all directions. Capillary effect is not specific to a cylindrical geometry and occurs as well when two plates are in close proximity. In the present invention both cylindrical pores and non-cylindrical channels created by close proximity of plates formed upon compression of the particles are present. According to Young-Laplace equation, the capillary rise (i.e. the length that fluid travels) is inversely proportional to the average diameter of the capillary:

$$L \sim \frac{1}{d}$$

Where L is the length of the capillary rise, and d is the diameter of a capillary. Within the range of capillary flow of $10^{-2}$ to $10^2$ microns, the more narrow the capillary, the higher water travels.

In the case of loose, i.e. unpacked or uncondensed, particles, water comes into contact with each particle passively or by gravity. In contrast, in the case of the packed particles of the present invention, it is believed that the interstitial pores draw water actively to wet the particle surfaces.

The pore volume of the interstitial pores created by the packing of the particles is effective to absorb the liquid at the increased rate of absorption provided by the desired median pore diameter. The actual pore volume necessary to facilitate absorption of the liquid will depend in part on the relative concentration of the liquid and particles and the consistency sought upon hydration of the packed particles.

The combination of the increased absorption rate of the liquid into the interstitial pores provided by the median pore diameter and the pore volume formed upon packing of the particles provides improved wetting and swelling of the plurality of particles when placed in contact with the liquid, when compared to wetting and swelling of a plurality of loose particles of the same material by the same liquid. The actual pore volume and median pore diameter that is effective in providing such improved properties may depend on the material comprising the particles, as well as the intended use and consistency of the hydrated particles.

These improved properties of the plurality of packed particles of the present invention provides improved dry hemostatic compositions that are to be reconstituted at the site of use by a medical practitioner just prior to use, or that are to be placed directly on or into a wound or surgical site of the body requiring hemostasis. In certain embodiments, improved hemostatic properties are noted as disclosed herein below.

In the case of the packed particles or compositions to be reconstituted on site prior to use, mixing of the dry compositions comprising the plurality of packed particles with, e.g., a saline solution is improved such that less mechanical force and time are required to form a consistent, substantially homogenous hemostatic paste. Such compositions of the present invention maintain desired physical properties effective to provide flowability, extrudability and/or injectability at the point and time of use. In addition, due to reduced handling of the compositions by medical practitioners at the point of use, issues concerning compromising sterility of the hemostatic composition may be avoided or reduced.

In the case of dry hemostatic packed particles or compositions that are to be placed directly on or into a wound or surgical site, increased wetting and swelling of the hemostatic composition by physiological fluids of the body may provide significant improvements in the time to hemostasis. Such embodiments also are more conducive to use with certain medical devices suitable for and used to apply hemostatic compositions to a wound or surgical site. In such cases, the hemostatic composition may be applied topically, for instance to a puncture site of the body such as may be created by catherization. The composition also may be placed at least partially into a tissue tract of the body.

Hemostatic compositions of the present invention may consist of, or consist essentially of the plurality of packed particles, or may further comprise effective amounts of functional additives. By "functional additive", it is meant that the additive provides some physical, biological or therapeutic affect to the composition. By "effective amount", it is meant that amount necessary to provide to the compositions those functional properties for which the additive is being added. The effective amount also is limited by the maximum amount that may be added without causing detrimental physical or biological affects.

The variety of biological agents that can be used in conjunction with the plurality of packed particles of the invention is vast. In general, biological agents which may be administered via hemostatic compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and hemostatic agents, such as prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having hemostatic activity.

In addition, binders or other additives to aid in processing of the packed particles may be added. Such binders or additives may include, but are not limited to, candelilla wax, starch, cellulose, hydroxyl propyl methyl cellulose, polyethylene glycol, polyethylene oxide or poloxamer. Inorganic or acidic salts, such as sodium chloride, sodium phosphate, and sodium acetate, can be added to accelerate the hydration process.

Packed particles and compositions of the present invention may be prepared in various shapes, forms and sizes. They may be in the form of plugs, disks, rods, tubes, conical cylinders, spheres, half spheres, tablets, pellets, granules, or even fine particulates. The compressed structures so formed exhibit improved properties of wetability and/or water-swellability when compared to hemostatic compositions of uncondensed/loose particles. Compositions of the present invention may be used as is or mixed with saline, filled into a medical device, such as a syringe or other known applicators used to dispense flowable hemostatic compositions, and the device containing the composition sterilized by ionizing irradiation.

In certain embodiments of the present inventions the particles and/or compositions may be irradiated with a level of, e.g. ionizing irradiation, so as to provide sterility to the materials. Such irradiation may include e-beam or gamma irradiation. The level of irradiation and conditions of sterilization, including the time that the compositions are irradiated, are those that provide sterile compositions, as defined herein. Sterilization conditions are similar to those currently utilized in the preparation of hemostatic loose powders currently available. Once having the benefit of this disclosure, one skilled in the art will be able to readily determine the level of irradiation necessary to provide sterile compositions.

A variety of biocompatible natural, semi-synthetic or synthetic polymers may be used to form the solid particles used in the present invention. The polymer selected must be substantially insoluble in the liquid used to reconstitute the composition or in physiological fluids. Preferably, water-insoluble biodegradable polymers used are wettable, water-swellable and provide mechanical, chemical and/or biological hemostatic activity. Polymers that may be used include, without limitation, proteins and polysaccharides. Polysaccharides that may be used include oxidized cellulose, chitosan, chitin, alginate, oxidized alginate, oxidized starch and diethylaminoethyl cellulose beads.

The biocompatible polymer used to prepare the particles in certain embodiments is a crosslinked or denatured protein, such as gelatin, collagen, fibrinogen or fibronectin. A collagen powder suitable for use in the present inventions may be prepared by milling INSTAT® topical absorbable hemostatic pad to the desired particle size. Collagen used to make INSTAT® pads is chemically crosslinked with diisocyanate. A gelatin powder suitable for use in the present inventions is Surgifoam® hemostatic gelatin powder. Surgifoam® powder is a dehydrothermally crosslinked gelatin powder. By "dehydrothermally crosslinked", it is meant that the gelatin material is heated above 100° C. under vacuum to form cross-links by removing water. The cross-links are due to ester or amide formation between functional groups. Both INSTAT and Surgifoam are prepared by first forming a proteinaceous sponge and then milling the sponge into loose particles having a median diameter of from about 40 microns to about 1,200 microns, more preferably from about 100 microns to about 1,000 microns, as determined by laser diffraction. The milling process involves strong shearing action, producing particles of a ribbon-like nature. The ribbon-structured particles are not readily free-flowing due to entanglement of the particles and to the high aspect ratio of the particles, yet are readily hydrated. Both INSTATE topical absorbable hemostatic pad and Surgifoam® hemostatic gelatin powder are available from Johnson & Johnson Wound Management, a division of Ethicon, Inc., Somerville N.J.

As indicated herein, the interstitial pore volume of the plurality of packed particles and the median interstitial pore diameter are key in providing both hemostatic and physical properties as described herein to the compositions of the present invention.

Where the particles comprise a protein such as collagen or gelatin, the density of the compressed particles of the present invention may be from about 0.2 to about 0.8 grams per cubic centimeters. The median interstitial pore diameter of the condensed protein particles generally may be from about 5 to about 50 microns, and in some embodiments from about 7 to about 20 microns. The interstitial pore volume in such embodiments may be from about 0.4 to about 10 cubic centimeters per gram, and in some embodiments from about 1 to about 5 cubic centimeters per gram.

Where the plurality of packed particles comprises collagen particles, the median interstitial pore diameter may be from about 8 to about 20 microns, more preferably from about 8 to about 10 microns. The interstitial pore volume of embodiments using collagen may be from about 1.5 to about 10 cubic centimeters per gram, and in some embodiments from about 2 to about 5 cubic centimeters per gram.

Figure 2:
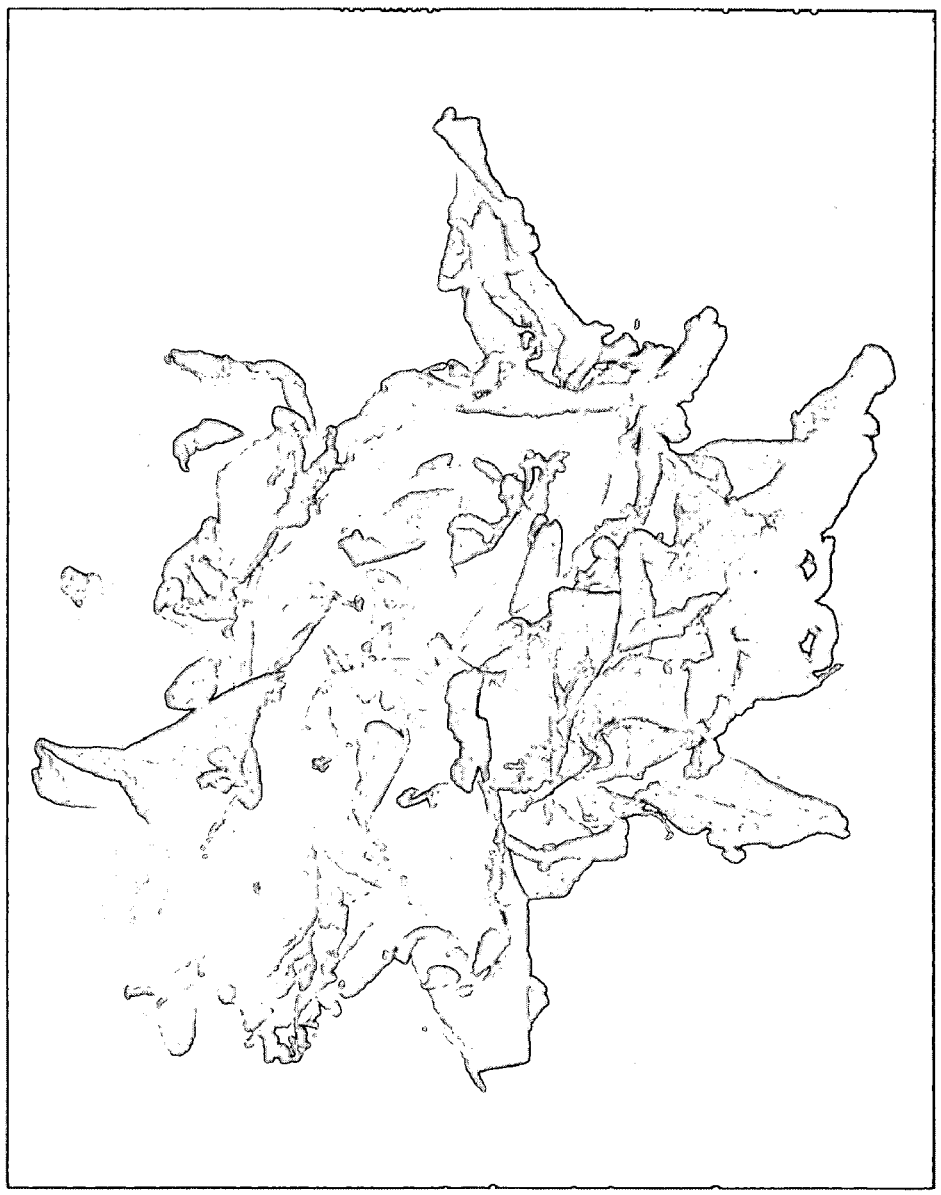
FIG. 2 is an image produced by scanning electron microscopy (200×) of a plurality of loose collagen particles.
Figure 3:
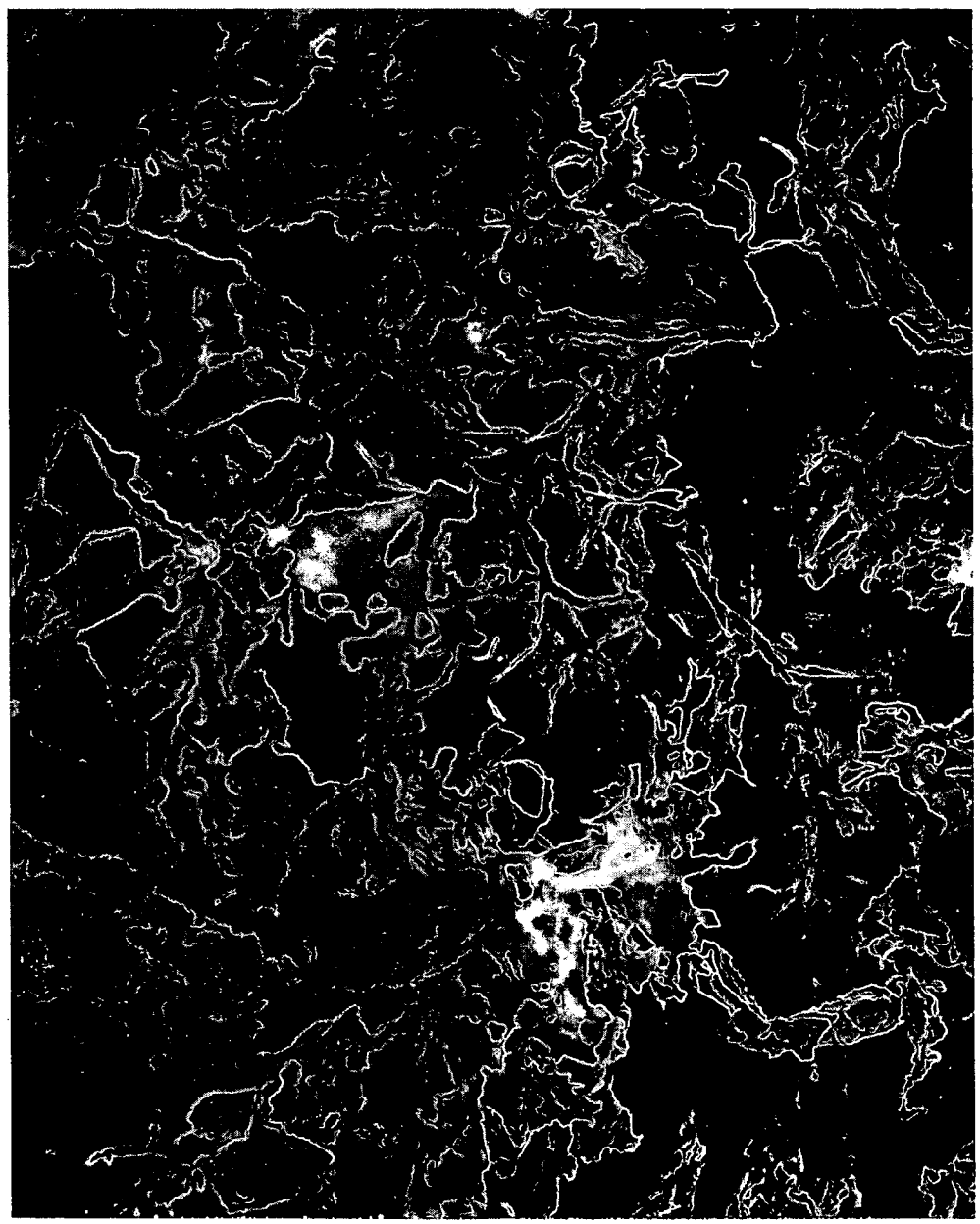
FIG. 3 is an image produced by scanning electron microscopy (100×) of a plurality of packed collagen particles according to the present invention.
Figure 4:
FIG. 4 is an image produced by scanning electron microscopy (750×) of a plurality of packed collagen particles according to the present invention.

FIGS. 1-4 show both non-compressed collagen particles and packed/condensed particles according to the invention formed at 5-ton compression force. FIG. 1 is an image produced by scanning electron microscopy (500×) of a collagen particle that has not undergone compression. As noted, the particle itself is substantially free of pores. FIG. 2 shows a plurality of loose, i.e. non-compressed, collagen particles (200×). Large spaces may be noted between the individual particles. FIGS. 3 (100×) and 4 (750×) show packed particles of the present invention formed by compressing loose collagen particles at a force of 5 tons. Interstitial pores are observed. In addition, deformation of the individual particles may be noted, thus forming a portion of the interstitial pore volume of the packed particles.

Where the plurality of packed particles comprises gelatin particles, the median interstitial pore diameter may be from about 7 to about 20 microns, more preferably from about 7 to about 15 microns. The interstitial pore volume of embodiments using gelatin may be from about 1 to about 4 cubic centimeters per gram, and in some embodiments from about 1 to about 2 cubic centimeters per gram.

Figure 5:
FIG. 5 is an image produced by scanning electron microscopy (2000×) of a gelatin particle.
Figure 6:
FIG. 6 is an image produced by scanning electron microscopy (100×) of a plurality of loose gelatin particles.
Figure 7:
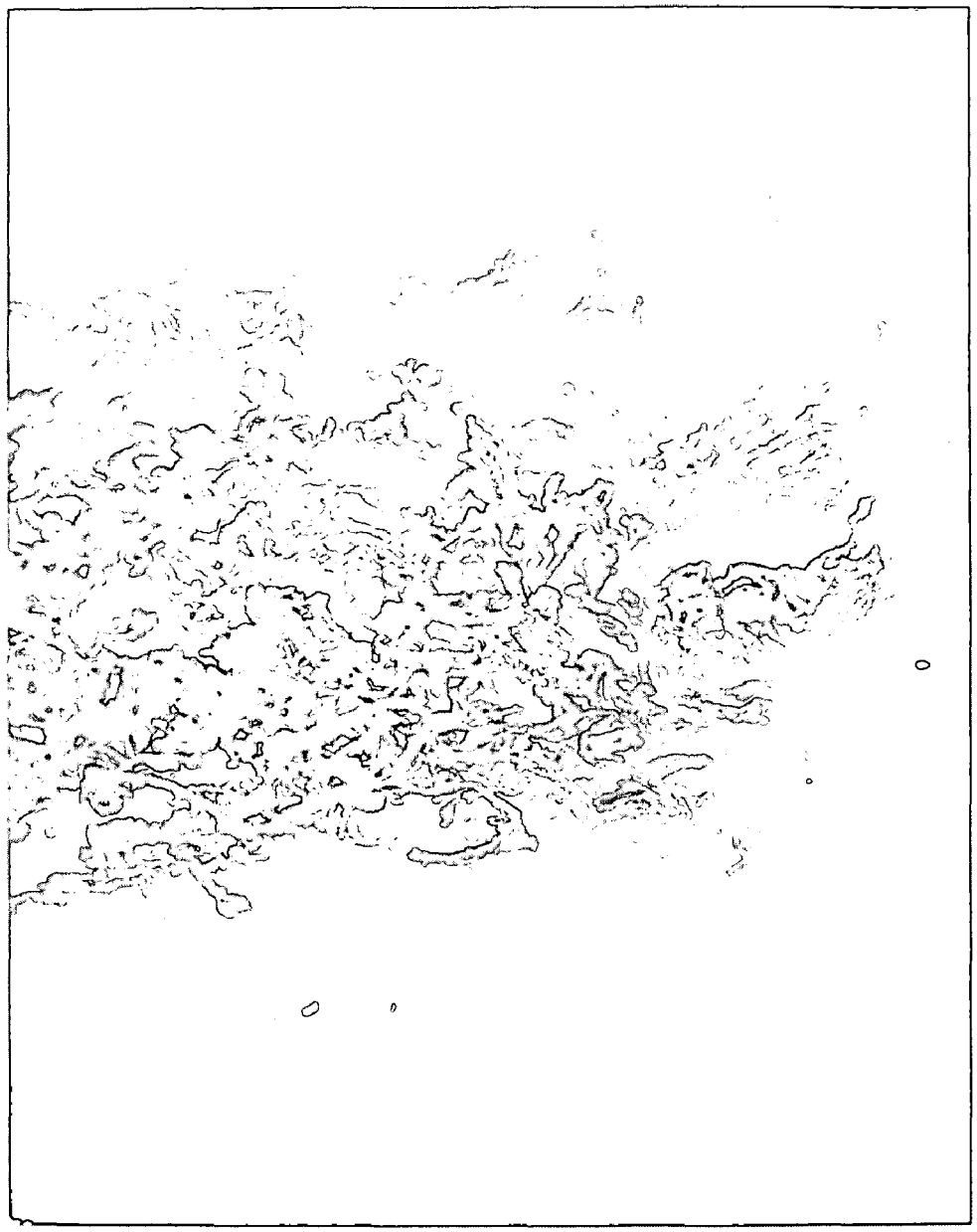
FIG. 7 is an image produced by scanning electron microscopy (50×) of a plurality of packed gelatin particles according to the present invention.

FIGS. 5-8 show both non-compressed gelatin particles and packed particles according to the invention formed at 3-ton compression force. FIG. 5 is an image produced by scanning electron microscopy (2,000×) of a gelatin particle that has not undergone compression. As noted, the particle itself is substantially free of pores. FIG. 6 shows a plurality of loose, i.e. non-compressed, gelatin particles (100×). Large spaces may be noted between the individual particles. FIGS. 7 (50×) and 8 (200×) show packed particles of the present invention formed by compressing loose gelatin particles at a force of 3 tons. Interstitial pores are observed. In addition, deformation of the individual particles may be noted, thus forming a portion of the interstitial pore volume of the packed particles.

The plurality of packed particles and/or compositions of the present invention may be prepared in different shapes, forms and sizes, depending on the contemplated use and method of delivery of the packed particles or composition. In certain embodiments, the body of packed particles may be made by mechanical compaction or compression at pre-determined force, or by extrusion. Depending on shape, form and size desired for the contemplated use, different molds may be used to achieve the desired hemostatic body of particles or compositions.

After formation of the body of packed particles as above, the packed particles may further be subjected to a freeze-drying process, such as lyophilization, in order to remove residual water that may be trapped in the interstitial pores. The formed body of packed particles may be placed in a vacuum chamber at a temperature of −50° C. in order to freeze residual water. A vacuum effective to remove the water is established and the material is left in the chamber for a time effective to facilitate removal of the frozen water, for example about 8 hours. The temperature is then returned to about 25° C. and the materials removed. While the particular conditions noted are effective to remove the trapped water, other conditions may be used as well and one skilled in the art would be able to ascertain what conditions would be effective once having the benefit of this disclosure. While lyophilization of the packed particles is not required in the present invention, it may provide improved consistency of the final body of packed particles or compositions of the present invention. In studies conducted, it was noted that the maximum number of transfers required to reconstitute the packed particles, as described herein, was reduced upon lyophilization, while the average number of transfers required was substantially the same.

The plurality of packed particles and/or compositions of the present invention in desired shapes, forms and sizes may also be obtained through a freeze-drying process, e.g. lyophilization. In this case, a dispersion of the loose particles in a liquid in which the particles are insoluble is prepared in the form of a paste or slurry of a density effective to provide the proper packing properties of pore volume and median pore diameter. The dispersion is then frozen to immobilize the particles in the frozen liquid phase and the liquid phase is then removed by vacuum drying, thus providing the plurality of packed particles.

Once prepared as above, the packed particles and/or compositions may be placed in a medical device, such as a syringe, and reconstituted into a flowable or injectable slurry just prior to use. As opposed to conventional loose, unpacked powders currently used, when mixed with a saline or thrombin solution, the packed particles and compositions of the present invention readily expand and afford a homogeneous paste without excessive mechanical mixing force and in a shorter period of time.

By way of explanation, although not intending to limit the scope of the invention, it is believed that when the conventional loose powder is first mixed with a liquid, the powder first in contact with the liquid hydrates rapidly to form a gel. The gel blocks any further penetration of the liquid into the body of powder, thus decreasing the amount of liquid available to wet the bulk of the remaining powder. It is believed that one reason this gel-blocking phenomenon occurs in a syringe is that the apparent density of the powder is too low, which means for a given powder weight, it occupies too much volume. Since the powder forms a gel so fast, the gel blocks channels from further penetration of the liquid into the spaces between the loose particles. Therefore, a homogeneous paste may not be achieved without increased mechanical mixing force and mixing time, and in some cases may not be achieved at all.

For the same powder/solution ration (weight/volume), increasing the apparent density of powder, thus providing desired interstitial pore volume and median diameter in the more dense material, as in the present invention, minimizes or eliminates the gel-blocking phenomenon and provides a homogeneous paste. In this scenario, when a dense body of packed particles is mixed with saline or thrombin solution, for example, the packed particles absorb more of the liquid into the interstitial pores, and then hydration of the packed particles follows. This sequence of action ensures a rapid formation of a homogeneous paste with minimum work.

Materials of the invention also may be applied directly to the wound or surgical site without reconstitution by a liquid. In this case, the same phenomenon causes physiological fluids, such as blood, to absorb into the interstitial pores and then to form a gel, thus minimizing gel blocking. In certain embodiments, significant reduction in the time required to provide hemostasis is observed.

Medical devices in which the hemostatic compositions of the present invention may be utilized include any device currently being used to apply a flowable or injectable hemostatic paste or slurry to a site of the body requiring hemostasis. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

Once combined with the medical device, the device containing the hemostatic composition may be sterilized, preferably by ionizing radiation. More preferably, sterilization is by gamma irradiation. It has been found that such a composition and device according to this invention can withstand sterilizing radiation without detrimentally affecting the mechanical properties or hemostatic efficacy post irradiation.

While the following examples demonstrate certain embodiments of the invention, they are not to be interpreted as limiting the scope of the invention, but rather as contributing to a complete description of the invention.

Example 1

A total of ten samples of packed particles were prepared as follows. 0.5 gram of dry, non-sterile, milled, absorbable hemostatic collagen powder was placed into a 1.25-inch diameter mold. A cylindrical die (¼ inch) was inserted into the mold. A Carver® hydraulic press was used to compress the die into the mold with forces ranging from 1 to 5 tons. Two samples were compressed at each load. The force was maintained for 2 minutes and then was released in order to remove the die from the mold. The bottom plate of the mold was subsequently removed. The dry discs so formed were separated by pressing the die through the mold. The resulting discs were placed on a cutting surface and cut into small pellets in the shape of square diamonds and squares (1/16-1/8") using a rotary cutter. The density, pore volume and median pore diameter were determined by mercury intrusion porosimetry methods as noted by S. Westermarck, in "Use of Mercury Porosimetry and Nitrogen Adsorption in Characterisation of the Pore Structure of Mannitol and microcrystalline Cellulose Powders, Granules and Tablets", Academic Dissertation, U. of Helsinki, Finland, November 2000, using an AMP-60K-A-1 mercury intrusion unit. The maximum pressure was set for 30,000 psi. This fully computerized unit is capable of measuring the intrusion of the mercury liquid at very low-pressure readings of less than 1 psi up to 60,000 psi. This wide pressure range translates to a porosity range of 250 µm to 0.070 µm. The blank run normalizes out other factors, such as, the compression of the mercury. It is noted that measurements could not be made for non-compressed, loose particles due to the powder-like consistency of the materials.

One gram of the cut discs prepared at the respective forces was then placed into a 12 cubic centimeter Monoject luer syringe. Five milliliters of a saline solution was placed into a second syringe. The two syringes were connected one to the other via an interlocking luer. The saline and particles were then transferred back and forth until a consistent, substantially homogenous paste was formed. The number of transfers required to prepare the substantially homogenous paste was recorded in Table 1.

Additional discs compressed at 3 ton were sterilized by gamma irradiation at 30 Kgy. The number of transfers required to prepare the homogenous paste and the hemostatic properties were compared to samples that had not undergone sterilization and found to be unchanged, thus indicating stability with respect to sterilization and hemostatic effectiveness.

TABLE 1

| Compression Force (ton) | Density (g/cm$^3$) | Pore Volume (cm$^3$/g) | Median Pore diameter (micron) | Relative Theoretical Capillary Rise | Number of transfers |
|---|---|---|---|---|---|
| 0 | 0.04 | N/A | N/A | N/A | >35 |
| 1 | 0.29 | 7.34 | 44.0 | 0.02 | 13 |
| 2 | 0.35 | 4.17 | 16.0 | 0.06 | 7 |
| 3 | 0.46 | 1.89 | 8.6 | 0.12 | 6 |
| 4 | 0.53 | 1.84 | 8.5 | 0.12 | 5 |
| 5 | 0.74 | 1.96 | 9.0 | 0.11 | 5 |

As shown in Table 1, increasing the force applied to compress the collagen particles increases the density of the plurality of packed particles, while decreasing the pore volume of the packed powder particles and the median diameter of the pores themselves. The unique combination of pore volume and pore diameter results in an increase in capillary rise, thus allowing the liquid to penetrate faster into progressively smaller diameter pores. The enhanced penetration of the liquid into the pores in turn provides for enhanced wetability of the particles by the solution and decreases the number of transfers required to prepare a consistent and homogeneous paste within the syringe.

Example 2A

Hemostatic Performance of Compressed, Non-Hydrated Discs in Porcine Splenic Incision Model A porcine spleen incision model was used for hemostasis evaluation of non-hydrated compressed discs prepared in Example 1. A linear incision of 1.5 cm with a depth of 0.3 cm was made with a surgical blade on a porcine spleen. The discs were applied directly onto the incision sites. After application of the test article, digital tamponade was applied to the incision for 2 minutes. The hemostasis was then evaluated. Additional applications of digital tamponade for 30 seconds each time were used until complete hemostasis was achieved. Fabrics failing to provide hemostasis within 12 minutes were considered to be failures. Table 2 lists the results of the evaluation.

Example 2B

In Vivo Hemostatic Performance of Materials Prepared Above in Porcine Splenic Biopsy Punch Model A porcine spleen biopsy punch model was used for evaluation of the hemostatic properties of homogenous pastes formed by additional of the saline to the discs prepared in Example 1. A 6-mm biopsy punch was used to cut a tissue flap 3 mm deep. The tissue flap was cut out and 0.4 ml of the test materials was applied to the wound site. Manual compression was held over the wound site for 2 minutes. The wound site was then observed for up to 3 minutes for signs of bleeding. If bleeding was observed, additional applications of manual compression for 30 seconds each time were used until complete hemostasis was achieved. Table 2 lists the results of the evaluation. Results are represented as an average values for all samples tested.

TABLE 2

| Compression Force (ton) | Time to Hemostasis (mins:seconds) | |
|---|---|---|
| | 2A Non-hydrated pellet | 2B Hydrated paste |
| 0 | 3:00 (n = 4) | N/A |
| 1 | 3:12 (n = 4) | 2:05 (n = 3) |
| 2 | 3:03 (n = 4) | 2:15 (n = 3) |
| 3 | 2:01 (n = 4) | 2:10 (n = 3) |
| 4 | 2:25 (n = 4) | 1:51 (n = 3) |
| 5 | 1:26 (n = 4) | 3:10 (n = 3) |

Example 3

Samples of packed particles were prepared as in Example 1 using crosslinked hemostatic gelatin powder, except that the force used to compact the gelatin particles was 3 ton. Density, pore volume, median pore diameter and capillary rise were determined as in Example 1 and recorded in Table 3.

TABLE 3

| Compression Force (ton) | Density (g/cm$^3$) | Pore Volume (cm$^3$/g) | Median Pore diameter (micron) | Relative Theoretical Capillary Rise | Number of transfers |
|---|---|---|---|---|---|
| 0 | 0.04 | N/A | N/A | N/A | N/A |
| 1 | 0.23 | 2.98 | 19.43 | 0.05 | 7 |
| 2 | 0.31 | 2.14 | 14.05 | 0.07 | 6 |
| 3 | 0.34 | 1.67 | 11.51 | 0.09 | 13 |
| 4 | 0.45 | 1.65 | 11.74 | 0.09 | >20 |
| 5 | 0.58 | 1.08 | 6.96 | 0.14 | N/A |

Example 4

Samples of packed particles were prepared as in Example 1 using one gram of crosslinked hemostatic gelatin powder mixed with 5000 IU of thrombin (Thrombogen-JMI®, Jones Pharma Incorporated, St. Louis, Mo.), except that the force used to compact the gelatin particles and thrombin powders was 2 tons. The pressure was applied after the two components were thoroughly mixed. The pellets prepared as described were cut into small squares with a razor blade. The squares (1 gram) were loaded into a 10-mL BD Syringe (Syringe I). A second syringe was loaded with 5 mL saline solution (Syringe II). Syringes I and II were connected via a luer lock. The saline in Syringe II was pushed into Syringe I. The content in Syringe I was transferred into Syringe II by pushing its plunger. The content was then transferred back-and-force between the two syringes to make a paste. After applying back-and-force action for 4 times, a homogeneous paste was formed. The paste was collected in Syringe I.

One mL of the paste was applied to a porcine spleen biopsy puncture defect model as described in example 2B. After an initial tamponade of 30 seconds, hemostasis was achieved. The test was repeated 5 times, and time to hemostasis was 30 seconds for each test.

Example 5

Samples of packed particles were prepared as in Example 1 using one gram of crosslinked hemostatic gelatin powder mixed with 5000 IU of thrombin (Thrombogen-JMI®, Jones Pharma Incorporated, St. Louis, Mo.), except that the force used to compact the gelatin particles and thrombin powders was 2 tons. The pressure was applied after the two components were thoroughly mixed. The pellets prepared as described were cut into small squares with a razor blade. The squares (1 gram) were loaded into a 10-mL BD Syringe (Syringe I). The syringe containing gelatin pellets was sterilized with Gamma irradiation at 25 KGy.

A second syringe was loaded with 5 mL saline solution (Syringe II). Syringes I and II were connected via a luer lock. The saline in Syringe II was pushed into Syringe I. The content in Syringe I was transferred into Syringe II by pushing its plunger. The content was then transferred back-and-force between the two syringes to make a paste. After applying back-and-force action for 4 times, a homogeneous paste was formed. The paste was collected in Syringe I.

One mL of such paste was applied to a porcine spleen biopsy puncture defect model as described in example 2B. After an initial tamponade of 30 seconds, hemostasis was achieved. The test was repeated 5 times. The time to hemostasis was 30 seconds for four tests, and 95 seconds for the remaining test. The average time to hemostasis was 43 seconds. It is believed that such a composition and device as well as thrombin therein according to this invention can withstand sterilizing radiation without detrimentally affecting the mechanical properties or hemostatic efficacy post irradiation.

We claim:

1. A hemostatic composition, comprising:
a plurality of compressed particles comprising interstitial pores having a pore volume and a median pore diameter effective to provide improved absorption of physiological fluids or an aqueous media into said interstitial pores when placed in contact therewith, compared to a plurality of unpacked particles of the same material, said particles comprising a biocompatible material and having an average diameter suitable for use in providing hemostasis to a site of a body of a mammal requiring hemostasis, and
wherein said pore volume of the hemostatic composition is from about 2 to about 5 cubic centimeters per gram and said median pore diameter is from about 8 to about 20 microns.

2. The composition of claim 1 wherein said biocompatible material suitable for use in providing hemostasis to the site of the body is selected from the group consisting of proteins and polysaccharides and said average particle diameter is from about 40 to about 1,200 microns.

3. The composition of claim 2 wherein said biocompatible material is selected from the group consisting of gelatin and collagen, said pore volume is from about 2 to about 5 cubic centimeters per gram and said median diameter is from about 8 to about 20 microns.

4. The composition of claim 2 wherein said biocompatible material is collagen, said pore volume is from about 2 to about 5 cubic centimeters per gram and said median pore diameter is from about 8 to about 20 microns.

5. The composition of claim 2 wherein said biocompatible material comprises gelatin, said pore volume is from about 2 to about 5 cubic centimeters per gram and said median pore diameter is from about 8 to about 20 microns.

6. The composition of claim 5 wherein said pore volume is from about 1 to about 2 cubic centimeters per gram and said median pore diameter is from about 8 to about 15 microns.

7. The composition of claim 1 wherein said particles are substantially non-porous.

8. The composition of claim 1 wherein said gelatin and collagen are crosslinked.

9. The composition of claim 1 further comprising an effective amount of a functional agent.

10. The composition of claim 1 wherein said composition is in the form of a plug, a pellet, a tablet, a disc, a rod, a tube, a conical cylinder, a sphere, a half-sphere or a granule.

* * * * *